United States Patent [19]
Böcker et al.

[11] Patent Number: 5,749,925
[45] Date of Patent: May 12, 1998

[54] DYEING OR PRINTING PROCESS WITH NEW AND KNOWN CATIONIC 4,5-DIHYDRO-1H-1,2,3-TRIAZOLIUM COMPOUNDS AS DYESTUFFS AND NEW CATIONIC 4,5-DIHYDRO-1H-1,2,3-TRIAZOLIUM COMPOUNDS

[75] Inventors: Thomas Böcker, Leichlingen; Horst Berneth, Leverkusen; Henry Giera, Bergisch Gladbach, all of Germany

[73] Assignee: Bayer Aktiengesellschaft, Leverkusen, Germany

[21] Appl. No.: 670,913

[22] Filed: Jun. 26, 1996

[30] Foreign Application Priority Data

Jul. 3, 1995 [DE] Germany .................. 195 24 133.9

[51] Int. Cl.$^6$ .................. D06P 1/42; D06P 3/76
[52] U.S. Cl. .................. 8/436; 8/655; 8/917; 8/918; 8/919; 8/927
[58] Field of Search .................. 8/436, 655, 916–927

[56] References Cited

U.S. PATENT DOCUMENTS 4,432,897  2/1984  Fürstenwerth.
5,356,857  10/1994  Vanmaele.

FOREIGN PATENT DOCUMENTS 0 053 751 A1  6/1982  European Pat. Off..

OTHER PUBLICATIONS

H. Hansen et al, Chem. Ber. vol. 112, pp. 445–691 (1979) abstract only.
H. Berneth et al., Liebigs Ann. Chem., pp. 285–290 (1980) abstract only.
K. Venkataramon, in "The Chemistry of Synthetic Dyes", vol. 4, pp. 288–291 (1971).

Primary Examiner—Margaret Einsmann
Attorney, Agent, or Firm—Sprung Kramer Schaefer & Briscoe

[57] ABSTRACT

4,5-Dihydro-1H-1,2,3-triazolium compounds of the formula (I)

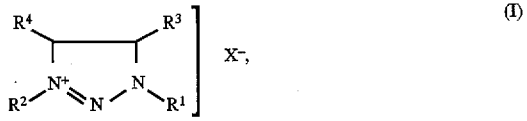

in which
R$^1$ and R$^2$ independently of one another denote $C_6$–$C_{14}$-aryl or a heterocyclic radical having up to 3 rings and up to 4 heteroatoms from the series consisting of O, S and N,
R$^3$ and R$^4$ independently of one another denote hydrogen, $C_1$–$C_{12}$-alkyl, $C_2$–$C_{12}$-alkenyl, $C_4$–$C_8$-cycloalkyl, $C_7$–$C_{17}$-aralkyl, $C_6$–$C_{14}$-aryl or nitrile or
R$^3$ and R$^4$ together denote a 2- to 5-membered C bridge, which can optionally be interrupted by up to two oxygen and/or nitrogen atoms, and
X$^-$ denotes an anion,
wherein all the alkyl, alkenyl, cycloalkyl, aralkyl and aryl radicals and fused and heterocyclic radicals present can optionally be substituted by nonionic substituents, carboxyl groups, ammonium groups and/or pyridinium groups, are used as dyestuffs.

New 4,5-dihydro-1H-1,2,3-triazolium compounds correspond to the formula (I), with the provisos that if R$^3$ and R$^4$ in each case denote hydrogen then in the case where R$^1$=4-methylphenyl R$^2$ does not represent 4-nitrophenyl, 4-methoxyphenyl or phenyl and R$^1$ and R$^2$ do not both simultaneously represent 4-methylphenyl, 4-nitrophenyl, 4-methoxyphenyl or phenyl.

8 Claims, No Drawings

DYEING OR PRINTING PROCESS WITH NEW AND KNOWN CATIONIC 4,5-DIHYDRO-IH-1,2,3-TRIAZOLIUM COMPOUNDS AS DYESTUFFS AND NEW CATIONIC 4,5-DIHYDRO-1H-1,2,3-TRIAZOLIUM COMPOUNDS

Some triazolium compounds and their UV spectra and voltametric measurement are known from Chem. Ber. 112, 445 to 461 (1979) and Liebigs Ann. Chem. 1980, 285 to 290.

It has now been found a dyeing or printing process which comprises to dye or to print with one or more 4,5-dihydro-1H-1,2,3-triazolium compounds of the formula (I)

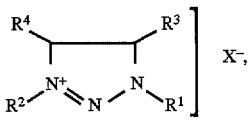

in which $R^1$ and $R^2$ independently of one another denote $C_6$–$C_{14}$-aryl or a heterocyclic radical having up to 3 rings and up to 4 heteroatoms from the series consisting of O, S and N, $R^3$ and $R^4$ independently of one another denote hydrogen, $C_1$–$C_{12}$-alkyl, $C_2$–$C_{12}$-alkenyl, $C_4$–$C_8$-cycloalkyl, $C_7$–$C_{17}$-aralkyl, $C_6$–$C_{14}$-aryl or nitrile or $R^3$ and $R^4$ together denote a 2- to 5-membered C bridge, which can optionally be interrupted by up to two oxygen and/or nitrogen atoms, and X⁻ denotes an anion, wherein all the alkyl, alkenyl, cycloalkyl, aralkyl and aryl radicals and fused and heterocyclic radicals present can optionally be substituted by nonionic substituents, carboxyl groups, ammonium groups and/or pyridinium groups, can be used as dyestuffs.

Alkyl radicals, including those in alkoxy and aralkyl radicals, can be straight-chain or branched.

Nonionic substituents are, for example, the non-dissociating substituents customary in dyestuff chemistry, such as cyano, hydroxyl, halogen, nitro, $C_1$–$C_{12}$-alkyl, $C_1$–$C_{12}$-monoalkylamino, di-$C_1$–$C_{12}$-alkylamino, $C_6$–$C_{12}$-arylamino, $C_7$–$C_{15}$-aralkyl-amino, $C_1$–$C_{12}$-alkoxy, phenyl, $C_1$–$C_{12}$-acylamino, $C_1$–$C_{12}$-alkoxycarbonyl, $C_1$–$C_{12}$-alkoxycarbonyloxy, $C_1$–$C_{12}$-alkamidocarbonyl, $C_1$–$C_{12}$-alkylsulfonyl, $C_6$–$C_{10}$-arylazo, aminocarbonyl, phenylsulphonyl, sulphonamide, sulphonamyl and ureido, which in their turn can optionally be substituted by hydroxyl, halogen, cyano and/or $C_1$–$C_6$-alkoxy.

X⁻ preferably represents a colourless organic or inorganic anion, for example fluoride, chloride, bromide, iodide, perchlorate, tetrafluoroborate, hydroxide, hydrogen sulphate, sulphate, dihydrogen phosphate, hydrogen phosphate, phosphate, bicarbonate, carbonate, methylsulphate, ethyl-sulphate, cyanate, thiocyanate, tri- or tetrachlorozincate, tetrachloroferrate or hexafluorosilicate, or an anion of a saturated or unsaturated aliphatic, cycloaliphatic, aromatic or heterocyclic carboxylic or sulphonic acid, for example formate, acetate, hydroxyacetate, cyanoacetate, propionate, hydroxypropionate, oxalate, citrate, lactate, tartrate, the anion of cyclohexanecarboxylic acid, phenylacetate, benzoate, the anion of nicotinic acid, methanesulphonate, ethanesulphonate, benzenesulphonate, chlorobenzenesulphonate and toluenesulphonate.

If the anion is a polyvalent anion, for example sulphate or oxalate, X⁻ in formula (I) represents one equivalent of such a polyvalent anion.

According to the invention, 4,5-dihydro-1H-1,2,3-triazolium compounds of the formula (I) are preferred in which $R^1$ and $R^2$ independently of one another denote phenyl, naphthyl, thienyl, thiazolyl, isothiazolyl, 1,2,4-thiadiazolyl, 1,3,4-thiadiazolyl, benzothiazolyl, benzisothiazolyl, pyrazolyl, imidazolyl, benzimidazolyl, oxazolyl, benzoxazolyl, 1,2,3-triazolyl, 1,2,4-triazolyl, indolyl or pyridyl, wherein these radicals can optionally be substituted by up to 5 radicals from the group consisting of $C_1$–$C_8$-alkyl, $C_1$–$C_8$-alkoxy, $C_6$–$C_{10}$-aryloxy, $C_6$–$C_{10}$-arylamino, $C_7$–$C_{12}$-aralkylamino, $C_1$–$C_8$-acylamino, $C_1$–$C_8$-acyloxy, $C_1$–$C_8$-monoalkylamino, di-$C_1$–$C_8$-alkylamino, $C_1$–$C_8$-alkoxycarbonyl, $C_1$–$C_8$-alkoxycarbonyloxy, $C_1$–$C_{12}$-alkamidocarbonyl, $C_1$–$C_{12}$-alkylsulphonyl, $C_6$–$C_{10}$-arylazo, aminocarbonyl, halogen, cyano, hydroxyl, nitro, phenylsulphonyl, sulphonamide, sulphonamyl and ureido, which in their turn can optionally be substituted by hydroxyl, halogen, cyano and/or $C_1$–$C_4$-alkoxy, $R^3$ and $R^4$ independently of one another in each case denote hydrogen, $C_1$–$C_8$-alkyl, allyl, cyclopentyl or cyclohexyl which are optionally substituted by hydroxyl, halogen, cyano, $C_1$–$C_4$-alkoxy, aminocarbonyl and/or $C_1$–$C_4$-alkoxycarbonyl, a benzyl, phenethyl, furyl, tetrahydrofurylmethyl, pyridyl, pyridylmethyl or pyridylethyl radical which are optionally substituted by halogen, cyano, $C_1$–$C_4$-alkyl and/or $C_1$–$C_4$-alkoxy, or a phenyl radical which is optionally substituted by halogen, cyano, $C_1$–$C_4$-alkyl or $C_1$–$C_4$-alkoxy or $R^3$ and $R^4$, together with the two carbon atoms in between, form a cyclobutane, cyclopentane, cyclohexane or cycloheptane ring which is optionally substituted by hydroxyl, halogen, cyano, $C_1$–$C_4$-alkoxy and/or aminocarbonyl and is optionally interrupted by a nitrogen atom, a tetrahydropyrrolidino or piperidino ring which is optionally substituted by hydroxyl, halogen, cyano, $C_1$–$C_4$-alkoxy and/or aminocarbonyl and is optionally interrupted by an oxygen atom, or a tetrahydrofuryl or tetrahydropyranyl ring which is optionally substituted by hydroxyl, halogen, cyano, $C_1$–$C_4$-alkoxy and/or aminocarbonyl and X⁻ denotes an anion.

Halogen preferably represents fluorine, chlorine and bromine.

According to the invention, 4,5-dihydro-1H-1,2,3-triazolium compounds of the formula (I) are particularly preferred in which $R^1$ and $R^2$ independently of one another denote phenyl, naphthyl, thienyl, thiazolyl, isothiazolyl, 1,2,4-thiadiazolyl, 1,3,4-thiadiazolyl, benzothiazolyl, benzisothiazolyl, imidazolyl, benzimidazolyl, benzoxazolyl, 1,2,4-triazolyl or pyridyl, wherein these radicals can optionally be substituted by up to 5 radicals from the group consisting of $C_1$–$C_4$-alkyl, $C_1$–$C_4$-alkoxy, $C_6$–$C_{10}$-aryloxy, $C_6$–$C_{10}$-arylamino, $C_7$–$C_{12}$-aralkylamino, $C_1$–$C_4$-acylamino, $C_1$–$C_4$-acyloxy, $C_1$–$C_4$-monoalkylamino, di-$C_1$–$C_4$-alkylamino, $C_1$–$C_4$-alkoxycarbonyl, $C_1$–$C_4$-alkoxycarbonyloxy, $C_1$–$C_4$-alkamidocarbonyl, $C_1$–$C_4$-alkylsulphonyl, $C_6$-arylazo, aminocarbonyl, halogen, cyano, hydroxyl, nitro, phenylsulphonyl, sulphonamide, sulphonylamyl and ureido, which in their turn can optionally be substituted by hydroxyl, halogen, cyano and/or $C_1$–$C_4$-alkoxy, $R^3$ and $R^4$ independently of one another in each case denote hydrogen or a $C_1$–$C_4$-alkyl radical which is optionally substituted by hydroxyl, halogen, cyano, $C_1$-$C_4$-alkoxy, aminocarbonyl and/or $C_1$-$C_4$-alkoxycarbonyl or $R^3$ and $R^4$, together with the two carbon atoms in between, denote a cyclopentane or cyclohexane ring which is optionally substituted by hydroxyl, halogen, cyano, $C_1$-$C_4$-alkoxy and/or aminocarbonyl and $X^-$ denotes an anion.

According to the invention, 4,5-dihydro-1H-1,2,3-triazolium compounds of the formula (I) are especially preferred which correspond to the formula (II)

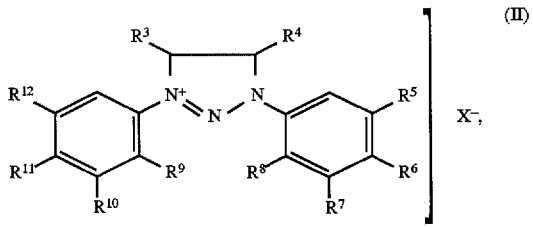

in which $R^3$ and $R^4$ independently of one another in each case denote hydrogen or a $C_1$-$C_4$-alkyl radical which is optionally substituted by hydroxyl, halogen, cyano, $C_1$-$C_4$-alkoxy, aminocarbonyl and/or $C_1$-$C_4$-alkoxycarbonyl or $R^3$ and $R^4$, together with the two carbon atoms in between, denote a cyclopentane or cyclohexane ring which is optionally substituted by hydroxyl, halogen, cyano, $C_1$-$C_4$-alkoxy and/or aminocarbonyl, $R^5$ to $R^{12}$ independently of one another in each case denote hydrogen or a $C_1$-$C_4$-alkyl, $C_1$-$C_4$-alkoxy, $C_6$-$C_{10}$-aryloxy, $C_6$-$C_{10}$-arylamino, $C_7$-$C_{12}$-aralkylamino, $C_1$-$C_4$-acylamino, $C_1$-$C_4$-acyloxy, $C_1$-$C_4$-monoalkylamino, di-$C_1$-$C_4$-alkylamino, $C_1$-$C_4$-alkoxycarbonyl, $C_1$-$C_4$-alkoxycarbonyloxy, $C_1$-$C_4$-alkamidocarbonyl, $C_1$-$C_4$-alkylsulphonyl or $C_6$-arylazo radical which is optionally substituted by hydroxyl, halogen, cyano and/or $C_1$-$C_4$-alkoxy, aminocarbonyl, halogen, cyano, hydroxyl, nitro, phenylsulphonyl, sulphonamide, sulphonamyl or ureido and $X^-$ denotes an anion.

According to the invention, 4,5-dihydro-1H-1,2,3-triazolium compounds of the formula (II) are preferred in which $R^3$ and $R^4$ independently of one another denote hydrogen or a $C_1$-$C_4$-alkyl radical, $R^5$ to $R^7$ and $R^{10}$ to $R^{12}$ independently of one another in each case denote hydrogen, a $C_1$-$C_4$-alkyl, $C_1$-$C_4$-alkoxy, phenoxy, phenylamino, phenyl-$C_1$-$C_4$-alkylamino, $C_1$-$C_4$-acylamino, $C_1$-$C_4$-acyloxy, $C_1$-$C_4$-monoalkyl-amino, di-$C_1$-$C_4$-dialkylamino, $C_1$-$C_4$-alkoxycarbonyl, $C_1$-$C_4$-alkoxycarbonyloxy, $C_1$-$C_4$-alkamidocarbonyl, $C_1$-$C_4$-alkylsulphonyl or phenylazo radical, aminocarbonyl, halogen, cyano, hydroxyl, nitro, phenylsulphonyl, sulphonamide, sulphonamyl or ureido, $R^8$ and $R^9$ independently of one another in each case denote hydrogen, $C_1$-$C_4$-alkyl, $C_1$-$C_4$-alkoxy, halogen, cyano or hydroxyl and $X^-$ denotes an anion.

According to the invention, 4,5-dihydro-1H-1,2,3-triazolium compounds of the formula (II) are particularly preferred in which $R^3$ and $R^4$ independently of one another denote hydrogen or methyl, $R^5$ and $R^{12}$, $R^6$ and $R^{11}$, $R^7$ and $R^{10}$, and $R^8$ and $R^9$, in each case as pairs, are identical and have one of the meanings given above as preferred in the case of formula (II) and $X^-$ denotes an anion.

According to the invention, 4,5-dihydro-1H-1,2,3-triazolium compounds of the formula (II) are especially preferred in which $R^3$ and $R^4$ independently of one another denote hydrogen or methyl, $R^6$ denotes hydrogen, methyl, methoxy, ethoxy, phenoxy, acetylamino, dimethylamino, diethylamino, methoxycarbonyl, ethoxycarbonyl, aminocarbonyl, chlorine, cyano or nitro, in the case where $R^3$ and $R^4$ in each case denote hydrogen, $R^{11}$ denotes ethoxy, phenoxy, acetylamino, dimethylamino, diethylamino, methoxycarbonyl, ethoxycarbonyl, aminocarbonyl, chlorine, cyano or nitro, and in the case where at least one of the radicals $R^3$ and $R^4$ is other than hydrogen $R^{11}$ additionally can also denote hydrogen, methyl, methoxy or nitro, $R^5$ and $R^{12}$, and $R^7$ and $R^{10}$, in each case as pairs, are identical and denote hydrogen, methyl, methoxy, ethoxy, phenoxy, acetylamino, dimethylamino, diethylamino, methoxycarbonyl, ethoxycarbonyl, aminocarbonyl, chlorine, cyano or nitro, $R^8$ and $R^9$ independently of one another in each case denote hydrogen, methyl or methoxy and $X^-$ denotes an anion.

4,5-Dihydro-1H-1,2,3-triazolium compounds of the formula (II) which are furthermore especially preferred are those in which $R^3$, $R^5$, $R^8$ $R^9$ and $R^{12}$ in each case denote hydrogen, $R^4$ denotes hydrogen or methyl, $R^6$ denotes methyl, methoxy, ethoxy, phenoxy, acetylamino, dimethylamino, diethylamino, methoxycarbonyl, ethoxycarbonyl or aminocarbonyl, in the case where $R^4$ denotes hydrogen, $R^{11}$ denotes ethoxy, phenoxy, acetylamino, dimethylamino, diethylamino, methoxycarbonyl, ethoxycarbonyl or aminocarbonyl, and in the case where $R^4$ denotes methyl, $R^{11}$ additionally can also denote hydrogen, methyl, methoxy or nitro, $R^7$ and $R^{10}$ independently of one another in each case denote hydrogen, methyl or methoxy and $X^-$ denotes an anion.

New 4,5-dihydro-1H-1,2,3-triazolium compounds of the formula (Ia)

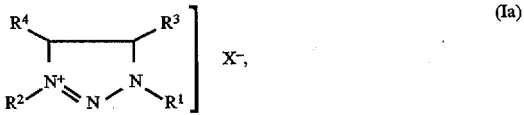

in which the symbols used have the meaning given in the case of formula (I), but with the provisos that if $R^3$ and $R^4$ in each case denote hydrogen then in the case where $R^1$=4-methylphenyl $R^2$ does not represent 4-nitrophenyl, 4-methoxyphenyl or phenyl and $R^1$ and $R^2$ do not both simultaneously represent 4-methylphenyl, 4-nitrophenyl, 4-methoxyphenyl or phenyl, have also been found.

The alkyl radicals, the nonionic substituents and the anion X⁻ can be of the same type as mentioned in the case of formula (I).

Preferred and particularly preferred 4,5-dihydro-1H-1,2,3-triazolium compounds of the formula (Ia) according to the invention are those in which the symbols used have the preferred and particularly preferred meaning mentioned in the case of formula (I), but in each case with the provisos that if $R^3$ and $R^4$ in each case denote hydrogen, in the case where $R^1$=4-methylphenyl $R^2$ does not represent 4-nitrophenyl, 4-methoxyphenyl or phenyl and $R^1$ and $R^2$ do not both simultaneously represent 4-methylphenyl, 4-nitrophenyl, 4-methoxyphenyl or phenyl.

Especially preferred 4,5-dihydro-1H-1,2,3-triazolium compounds of the formula (Ia) according to the invention correspond to the formula (IIa)

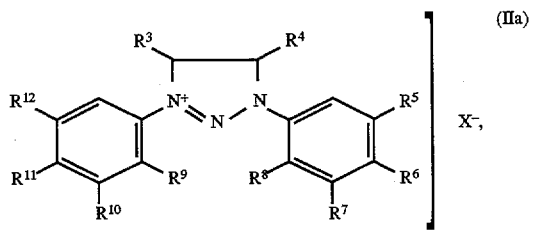

(IIa)

in which the symbols used have the meaning given in the case of formula (II), but with the proviso that if $R^3$ and $R^4$ in each case denote hydrogen, in the case where $R^6$=methyl $R^{11}$ does not represent nitro, methoxy or hydrogen and $R^6$ and $R^{11}$ do not both simultaneously represent methyl, nitro, methoxy or hydrogen.

Preferred 4,5-dihydro-1H-1,2,3-triazolium compounds of the formula (IIa) according to the invention are those in which the symbols used have the meaning given as preferred in the case of formula (II), with the proviso that if $R^3$ and $R^4$ in each case denote hydrogen, in the case where $R^6$=methyl $R^{11}$ does not represent nitro, methoxy or hydrogen and $R^6$ and $R^{11}$ do not both simultaneously represent methyl, nitro, methoxy or hydrogen.

Particularly and especially preferred 4,5-dihydro-1H-1,2,3-triazolium compounds of the formula (IIa) according to the invention are those in which the symbols used have, without proviso, the meaning given as particularly preferred and especially preferred in the case of formula (II).

A process for the preparation of 4,5-dihydro-1H-1,2,3-triazolium compounds of the formula (I), is for example, that a diazo component of the formula (III), $R^1$—NH₂      (III), in which $R^1$ has the broadest meaning given in the case of formula (I), to the secondary nitrogen atom of an activated coupling component of the formula (VI)

$R^2$—NH—CHR³—CHR⁴R¹³      (VI), in which $R^2$, $R^3$ and $R^4$ have the broadest meaning given in the case of formula (I) and $R^{13}$ denotes a leaving group, and then cyclizating the triazenes formed, of the formula (VII)

$R^1$—N=N—N(—CHR³—CHR⁴R¹³)—R²      (VII), in which $R^1$, $R^2$, $R^3$, $R^4$ and $R^{13}$ have the abovementioned meaning, to give 4,5-dihydro-1H-1,2,3-triazolium compounds of the formula (I).

The leaving group $R^{13}$ can be, for example, methanesulphonate, chloride, bromide, benzenesulphonate, p-toluenesulphonate, trifluoroacetate, acetate or sulphate.

The activated coupling components of the formula (VI) are obtainable in a manner known per se, for example by reaction of compounds of the formula (IV)

$R^2$—NH—CHR³—CHR⁴—OH      (IV), in which $R^2$, $R^3$ and $R^4$ have the broadest meaning given in the case of formula (I), with an acid halide, an acid anhydride or a mineral acid, for example with methanesulphonyl chloride, benzenesulphonyl chloride, p-toluenesulphonyl chloride, trifluoroacetyl chloride, trifluoroacetic anhydride, acetic anhydride, acetyl chloride, hydrogen bromide, hydrogen chloride or sulphuric acid.

A process for the preparation of 4,5-dihydro-1H-1,2,3-triazolium compounds of the formula (Ia) is, for example, that a diazo component of the formula (IIIa)

$R^2$—NH₂      (IIIa), in which $R^1$ has the broadest meaning given in the case of formula (Ia), coupling the diazotization product to the secondary nitrogen atom of a coupling component of the formula (IVa)

$R^2$—NH—CHR³—CHR⁴—OH      (IVa), in which $R^2$, $R^3$ and $R^4$ have the broadest meaning given in the case of formula (Ia), and then cyclizating the triazenes formed, of the formula (V)

$R^1$—N=N—N(—CHR³—CHR⁴13 OH)—$R^2$      (V), in which $R^1$, $R^2$, $R^3$ and $R^4$ have the broadest meaning given in the case of formula (Ia), intramolecularly by activation of the hydroxyl group to give 4,5-dihydro-1H-1,2,3-triazolium compounds of the formula (Ia).

The aromatic and heterocyclic diazo components of the formulae (III) and (IIIa) and aromatic and heterocyclic coupling components of the formulae (IV) and (IVa) are known, for example from Houben-Weyl, Methoden der Organischen Chemie [Methods of Organic Chemistry], Volume XI/1, pages 3 to 262 and 341 to 1025, or are obtainable analogously thereto.

The activation of the hydroxyl group can be carried out in a manner known per se, for example by reaction of the hydroxyl group with an acid halide or anhydride, for example with methanesulphonyl chloride, benzenesulphonyl chloride, p-toluenesulphonyl chloride, trifluoroacetyl chloride, trifluoroacetic anhydride, acetic anhydride or acetyl chloride.

Another process for the preparation of 4,5-dihydro-1H-1,2,3-triazolium compounds of the formula (I) is for example, that a diazo component of the formula (III), is diazotized, the diazotization product is coupled to the nitrogen atom of a coupling component of the formula (VIII)

$$R^2\text{—}NH_2 \quad (VIII),$$

in which

R² has the broadest meaning given in the case of formula (I), and reacting the triazene formed, of the formula (IX)

$$R^1\text{—}N{=}N\text{—}NH\text{—}R^2 \quad (IX),$$

in which

R¹ and R² have the abovementioned meaning, with compounds of the formula (X)

$$R^{15}\text{—}CHR^3\text{—}CHR^4R^{14} \quad (X),$$

in which

R³ and R⁴ have the broadest meaning given in the case of formula (I),

R¹⁴ represents a leaving group to be replaced nucleophilically and

R¹⁵ represents hydroxyl or a leaving group, and then cyclizating the products in the case where R¹⁵= hydroxyl after prior activation, as described above.

R¹⁴ and R¹⁵, the latter where it denotes a leaving group, can be, for example, of the same nature as mentioned for R¹³.

The diazotizations mentioned can be carried out in a manner known per se, for example in accordance with Houben-Weyl, Methoden der Organischen Chemie [Methods of Organic Chemistry], Volume X/3, pages 1 to 112 and E16a, pages 1052 to 1087. For these reactions it is possible to use, for example, sodium nitrite in aqueous mineral acid, for example hydrochloric acid or sulphuric acid or nitrosylsulphuric acid in 80 to 90% strength by weight phosphoric acid or in mixtures of such phosphoric acids with acetic acid, propionic acid and/or sulphuric acid.

The couplings mentioned to give the triazenes of the formulae (V), (VII) and (IX) can likewise be carried out in a manner known per se, for example in accordance with Houben-Weyl, Methoden der Organischen Chemie [Methods of Organic Chemistry], Volume X/3, pages 695 to 723 and E16a, pages 1186 to 1220.

The diazotizations and couplings can also be carried out simultaneously by other processes known per se, for example by reacting compounds of the formulae (III) and (IIIa) and compounds of the formulae (IV) or (IVa) together in an acid medium with, for example, sodium nitrite. Suitable acid media are, for example, aqueous mineral acids or organic acids or mixtures thereof, possible aqueous mineral acids being, for example, aqueous hydrochloric acid, sulphuric acid or phosphoric acid and possible organic acids being, for example, formic acid, acetic acid or propionic acid. Carbon dioxide liquefied under pressure can also serve as the acid medium.

The compounds of the formula (I) or (Ia) formed precipitate directly out of the solutions and can be isolated, for example, by filtration. They can be obtained as solid products which can be filtered off, if water-miscible solvents are used, by dilution with water and addition of water-soluble salts, such as sodium chloride or potassium chloride, if appropriate in the presence of zinc chloride. Highly pure compounds can be obtained, for example, by purification by chromatography over silica gel.

Preferred processes for dyeing and printing with 4,5-dihydro-1H-1,2,3-triazolium compounds of the formulae (I) and (Ia) according to the present invention are processes for dyeing and printing cationically dyeable fibres, preferably polymers and copolymers of acrylonitrile and dicyanoethylene, and acid-modified fibres of polyamide and polyester, fast colour shades being obtained. These triazolium compounds can also be used for dyeing and printing tannin-treated cellulose materials, paper, silk and leather. They are furthermore suitable for the preparation of writing liquids, stamping liquids, ball-point pen pastes and ink-jet inks and can also be used in flexographic printing.

Dyeing of, for example, polymers and copolymers of acrylonitrile can be carried out, for example, from a weakly acid liquor, the goods preferably being introduced into the dyebath at 40° to 60° C. and dyeing then being carried out at the boiling point. Dyeing can also be carried out under pressure at temperatures above 100° C. Furthermore, the compounds of the formulae (I) and (Ia) can be introduced into spinning solutions for the production of dyed fibres.

Dyeings with compounds of the formulae (I) and (Ia) on materials of polyacrylonitrile are distinguished by very good fastnesses to light, wet processing and rubbing and by a high affinity for the fibre.

Compounds of the formulae (I) and (Ia) can be used individually, as mixtures with one another or as mixtures with other dyestuffs.

Finally, the present invention relates to cationically dyeable fibres, tannin-treated cellulose materials, paper, silk, leather, writing liquids, stamping liquids, ball-point pen pastes and ink-jet inks, which are characterized in that they comprise at least one 4,5-dihydro-1H-1,2,3-triazolium compound of the formula (I) or (Ia).

Those compounds of the formulae (I) and (Ia) which are preferably, particularly preferably and especially preferably prepared and used for dyeing are those which are described as such in the description of the compounds.

EXAMPLES

Example 1

2.3 g of 3,4-dimethoxyaniline were diazotized in a mixture of 22 ml of water and 3.75 ml of concentrated hydrochloric acid at 0° to 5° C. by dropwise addition of 1.1 g of sodium nitrite, dissolved in 4 ml of water. The diazonium salt solution was added dropwise to a solution of 2.29 g of the coupling component of the formula (IV) where R²=p-phenoxyphenyl and R³=R⁴=hydrogen in 50 ml of methanol, 50 ml of ice/water and 9 g of sodium bicarbonate at 0° to 50° C. in the course of 15 minutes. When the addition had taken place, the mixture was subsequently stirred for 10 minutes and extracted immediately with methylene chloride. The organic phase was dried with sodium sulphate. The triazene of the formula (V) where R¹=3,4-dimethoxyphenyl, R²=p-phenoxyphenyl and R³=R⁴= hydrogen contained in the organic phase was then cyclized directly with methanesulphonic acid. For this, 1.68 g of diazabicyclononane (DABCO) were added to the organic phase and 1.16 ml of methanesulphonyl chloride, dissolved in 3 ml of methylene chloride, were slowly added dropwise at −10° C. After a reaction time of 60 minutes, the solution was concentrated. After purification by chromatography over silica gel using the mobile phase mixture of methylene chloride:methanol 4:1, 2.1 g (52%) of an orange-yellow powder were obtained. The product of the formula (II) where R³, R⁴, R⁵, R⁷, R⁸, R⁹ and R¹²=hydrogen, R⁶=phenoxy, R¹⁰=R¹¹=methoxy and X=Cl gave a $\lambda_{max}$ of 431 nm in methanol.

FAB-MS: 376 (M⁺).

¹H-NMR (CD₃OD): 2.69, 3.92, 3.97, 5.03, 7.08, 7.15, 7.18, 7.22, 7.28, 7.38, 7.43 and 7.78 ppm.

Example 2

2.25 g of p-aminoacetanilide were diazotized in a mixture of 22 ml of water and 3.75 ml of concentrated hydrochloric acid at 0° to 5° C. by dropwise addition of 1.1 g of sodium nitrite, dissolved in 4 ml of water. The diazonium salt solution was added dropwise to a solution of 1.67 g of the coupling component of the formula (IV) where $R^2$=p-methoxy and $R^3$=$R^4$=hydrogen in 50 ml of methanol, 50 ml of ice/water and 9 g of sodium bicarbonate at 0° to 5° C. in the course of 15 minutes. When the addition was complete, the mixture was subsequently stirred for 10 minutes and then filtered with suction. The triazene of the formula (V) isolated, where $R^1$=p-acetaminophenyl, $R^2$=p-methoxyphenyl and $R^3$=$R^4$=hydrogen, was then dissolved in acetonitrile and cyclized analogously to Example 1. The precipitate which had separated out was filtered off with suction. After purification by chromatography over silica gel using the mobile phase mixture of methylene chloride:methanol 4:1, 2.4 g (69%) of an orange powder were obtained. The product of the formula (II) where $R^3$, $R^4$, $R^5$, $R^7$, $R^8$, $R^9$, $R^{10}$ and $R^{12}$=hydrogen, $R^6$=methoxy, $R^{11}$=acetamino and X=Cl gave a $\lambda_{max}$ of 426 nm in methanol.

FAB-MS: 311 ($M^+$).

$^1$H-NMR (CD$_3$OD): 2.16, 2.69, 3.90, 5.01, 7.17 and 7.70 ppm.

Example 3

9 g of p-anisidine were diazotized in a mixture of 50 ml of water and 20 ml of concentrated hydrochloric acid at 0° to 5° C. by dropwise addition of 18 ml of 30% strength by weight sodium nitrite solution. This diazonium salt solution was added dropwise to a solution of 20.4 g of the hydrobromide of the activated coupling component of the formula (VI) where $R^2$=phenyl, $R^3$=$R^4$=hydrogen and $R^{13}$=bromine in 125 ml of methanol, 125 ml of water and 46 g of sodium bicarbonate at 0° to 5° C. in the course of 30 minutes. After the mixture had been stirred overnight at room temperature, it was filtered with suction and the residue was washed with 200 ml of water. 60 ml of 2 molar aqueous zinc chloride solution were added to the yellow mother liquor and the precipitate was filtered off with suction and dried. 7.4 g (24% of theory) of powder of the formula (II) where $R^6$=methoxy, $R^3$ to $R^5$ and $R^7$ to $R^{12}$=hydrogen and $X^-$=ZnCl$_3^-$ were obtained. A $\lambda_{max}$ of 407.5 nm resulted in ethanol/glacial acetic acid.

$^1$H-NMR (CD$_3$OD): 3.90, 5.09, 7.08, 7.52, 7.63 and 7.77 ppm.

The activated coupling component of the formula (VI) was prepared as follows:

310 ml of 48% strength by weight hydrobromic acid were added dropwise to 100 g of N-(2-hydroxyethyl)-aniline at 0° C. The mixture was then heated to the boiling point and distilled over a packed column until the temperature at which the distillate passed over had reached 125° C. At this temperature at which the distillate passed over, a total of 347 g of distillate had been distilled off. The distillate was then cooled to room temperature, diluted with 500 ml of acetone and filtered with suction. After drying, 103 g (50% of theory) of the hydrobromide of the activated coupling component of the formula (VI) wherein the radicals had the meaning mentioned above for the active coupling component were obtained as colourless crystals of melting point 135° to 137° C.

Example 4

The procedure was as in Example 3, but 17.9 g of the activated coupling component of the formula (VI) where $R^2$=4-methoxyphenyl, $R^3$=$R^4$=hydrogen and $R^{13}$=O—SO$_2$—OH were employed. 13.2 g (40% of theory) of yellow powder of the formula (II) where $R^6$=$R^{11}$=methoxy, $R^3$ to $R^5$, $R^7$ to $R^{10}$ and $R^{12}$=hydrogen and $X^-$=ZnCl$_3^-$ were obtained. A $\lambda_{max}$ of 423 nm resulted in methanol.

FAB-MS: 284 ($M^+$).

$^1$H-NMR (CD$_3$OD): 2.69, 3.90, 4.99, 7.17 and 7.72 ppm.

The activated coupling component of the formula (VI) was prepared as follows:

4.5 g of N-(2-hydroxyethyl)-4-methoxyaniline were introduced into 8ml of concentrated sulphuric acid at 0° C. for 24 hours and then discharged onto 150 g of ice. The solution was brought to pH=4.5 with 8 ml of 45% strength by weight aqueous sodium hydroxide solution. After the mixture had been stirred overnight, it was filtered with suction. 4.4 g (66% of theory) of the activated coupling component of the formula (VI) wherein the radicals had the meaning given above for the active coupling component were obtained as colourless crystals. The mass of 247 is found in the mass spectrum (FAB).

Example 5

61.6 g of p-anisidine were initially introduced into 170 g of ice and 250 ml of water, and 76.5 g of concentrated hydrochloric acid were added. A solution of 17.4 g of sodium nitrite in 42 ml of water was added dropwise at 0° to 5° C. in the course of 15 minutes. A further solution of 70.5 g of sodium acetate in 135 ml of water was added dropwise in the course of 10 minutes. After the mixture had been stirred at room temperature for 2 hours, it was filtered with suction and the residue was washed with ice-water. After drying, 50.4 g (78%) of yellow powder of the triazene of the formula (IX) where $R^1$=$R^2$=p-methoxyphenyl remained.

2.6 g of triazene of the formula (IX) where $R^1$=$R^2$=p-methoxyphenyl were heated under reflux in 25 ml of tert-butanol with 2.3 g of potassium tert-butylate for 15 minutes. After dropwise addition of 1.6 g of chloroethanol, the mixture was heated for a further two hours. After cooling to 10° C., 3.5 g of benzenesulphonyl chloride and 2.8 ml of triethylamine were added dropwise in succession and the mixture was stirred at room temperature for 2 hours. After filtration with suction and drying, 2.8 g (63%) of yellow-orange powder of the formula (II) where $R^3$, $R^4$, $R^5$, $R^7$, $R^8$, $R^9$, $R^{10}$ and $R^{12}$=hydrogen, $R^6$=$R^{11}$=methoxy and X=benzenesulphonate were obtained from the orange-coloured suspension.

The analytical data correspond to those given in Example 4.

Examples 6 to 97

The procedure was analogous to Examples 1 to 5 and produced the following dyestuffs of the formula (I) wherein $R^3$ and $R^4$, unless stated otherwise, denote hydrogen and $X^-$, unless stated otherwise, denotes chloride.

| Example No. | Analogously to Example No. | R¹ | R² | $\lambda_{max}$ (nm) | FAB-MS (M⁺) |
|---|---|---|---|---|---|
| 6 | 1 | 4-Nitrophenyl | 4-Chlorophenyl | 397 | 304 |
| 7 | 1 | 4-Methoxyphenyl | 4-Cyanophenyl | 420 | 279 |
| 8 | 1 | 3,4-Dichlorophenyl | 4-Phenoxyphenyl | 410 | 385 |
| 9 | 1 | 3,5-Dimethoxyphenyl | 3,4-Dichlorophenyl | 395 | 353 |
| 10 | 1 | 4-Phenoxyphenyl | 4-Chlorophenyl | 409 | 351 |
| 11 | 1 | 4-Phenoxyphenyl | 4-Tolyl | 408 | 331 |
| 12 | 1 | 4-Methoxyphenyl | 4-Chlorophenyl | 415 | 288 |
| 13 | 1 | 4-Phenoxyphenyl | 4-Chlorophenyl | 409 | 351 |
| 14 | 1 | 4-Nitrophenyl | 4-Methoxyphenyl | 426 | 299 |
| 15 | 1 | 4-Nitrophenyl | 4-Phenoxyphenyl | 418 | 361 |
| 16 | 1 | 2,4-Dimethoxyphenyl | 4-Cyanophenyl | 415 | 309 |
| 17 | 1 | 4-Cyanophenyl | 4-Tolyl | 397 | 263 |
| 18 | 1 | 4-Phenoxyphenyl | 4-Cyanophenyl | 412 | 341 |
| 19 | 1 | 2,4-Dimethoxyphenyl | 3,4-Dichlorophenyl | 409 | 353 |
| 20 | 1 | 3,4-Dichlorophenyl | 4-Methoxyphenyl | 416 | 323 |
| 21 | 1 | 2,4-Dichlorophenyl | 4-Tolyl | 397 | 307 |
| 22 | 1 | 2,4-Dimethoxyphenyl | 2-Methyl-4-nitrophenyl | 403 | 343 |
| 23 | 1 | 2-Methyl-4-nitrophenyl | 4-Methoxyphenyl | 409 | 313 |
| 24 | 1 | 2-Methyl-4-nitrophenyl | 4-Tolyl | 388 | 297 |
| 25 | 1 | 2-(5-Diisopropylamino-1,3,4-thiadiazolyl) | 4-Methoxyphenyl | 474 | 364 |
| 26 | 1 | as for Example 25 | 4-Tolyl | 467 | 348 |
| 27 | 1 | as for Example 25 | 2,4-Dimethoxyphenyl | 462 | 390 |
| 28 | 1 | as for Example 25 | 4-Phenoxyphenyl | 474 | 424 |
| 29 | 1 | 2,4,6-Trimethylphenyl | (5-Diisopropylamino-1,3,4-thiadiazol)-2-yl | 432 | 374 |
| 30 | 1 | 2,4-Dimethoxyphenyl | 4-Methoxyphenyl | 406 | 314 |
| 31 | 1 | 4-Methoxyphenyl | 4-Methoxyphenyl | 424 | 284 |
| 32 | 1 | 2,4-Dimethoxyphenyl | 4-Nitrophenyl | 422 | 329 |
| 33 | 1 | 2,4-Dimethoxyphenyl | 4-Chlorophenyl | 403 | 319 |
| 34 | 1 | R¹ and R² as for Example 33 | R³ = Methyl | 406 | 333 |
| 35 | 1 | 3,4-Dichlorophenyl | 4-Phenoxyphenyl | 410 | 385 |
| 36 | 1 | R¹ = 3,4-Dichlorophenyl | R² = 4-Tolyl, R³ = Methyl | 391 | 321 |
| 37 | 1 | 1-[4-(4'-Chlorophenyl)-naphthyl] | 4-Phenoxyphenyl | 415 | 493 |
| 38 | 1 | as for Example 37 | 4-Tolyl | 394 | 415 |
| 39 | 1 | 1-(4-Nitronaphthyl) | 2,4-Dimethoxyphenyl | 405 | 379 |
| 40 | 1 | 2-Methoxyphenyl | 4-Methoxyphenyl | 398 | 284 |
| 41 | 1 | 3-Methoxyphenyl | 4-Methoxyphenyl | 413 | 284 |
| 42 | 1 | 3,4-Dimethoxyphenyl | 4-Methoxyphenyl | 433 | 314 |
| 43 | 1 | 2-Methyl-4-methoxyphenyl | 4-Methoxyphenyl | 398 | 334 |
| 44 | 1 | 3-Methoxy-4-methylphenyl | 4-Methoxyphenyl | 420 | 334 |
| 45 | 1 | 3,5-Dimethoxyphenyl | 4-Methoxyphenyl | 412 | 314 |
| 46 | 1 | 4-Phenoxyphenyl | 4-Methoxyphenyl | 420 | 346 |
| 47 | 1 | 3-Tolyl | 4-Methoxyphenyl | 407 | 268 |
| 48 | 1 | 3,4-Dimethoxyphenyl | 4-Phenoxyphenyl | 431 | 376 |
| 49 | 1 | 3-Methoxy-4-methylphenyl | 4-Phenoxyphenyl | 421 | 360 |
| 50 | 1 | 3-Methoxy-4-methylphenyl | 3,4-Dimethoxyphenyl | 412 | 328 |
| 51 | 1 | 3,4-Dimethoxyphenyl | 4-Tolyl | 424 | 334 |
| 52 | 1 | 3-Methoxy-4-methylphenyl | 4-Tolyl | 408 | 318 |
| 53 | 1 | 4-Methoxyphenyl | 4-Tolyl | 412 | 268 |
| 54 | 1 | 4-Tolyl | 4-Tolyl | 398 | 252 |
| 55 | 1 | 3,4-Dimethylphenyl | 4-Tolyl | 389 | 266 |
| 56 | 1 | 4-Ethoxycarbonylphenyl | 4-Tolyl | 398 | 310 |
| 57 | 2 | 4-Acetamidophenyl | 4-Tolyl | 415 | 255 |
| 58 | 2 | 4-Acetamidophenyl | 4-Methoxyphenyl | 426 | 311 |
| 59 | 1 | 4-Ethoxycarbonylphenyl | 4-Methoxyphenyl | 415 | 326 |
| 60 | 1 | 2,4-Dimethylphenyl | 4-Methoxyphenyl | 399 | 282 |
| 61 | 2 | 3,4-Dimethoxyphenyl | 4-Acetamidophenyl | 436 | 306 |
| 62 | 2 | 4-Phenoxyphenyl | 4-Acetamidophenyl | 420 | 373 |
| 63 | 2 | 2-Methoxyphenyl | 4-Acetamidophenyl | 415 | 311 |
| 64 | 2 | 2,4-Dimethylphenyl | 4-Acetamidophenyl | 395 | 309 |
| 65 | 2 | 3,5-Dimethoxyphenyl | 4-Acetamidophenyl | 415 | 341 |
| 66 | 2 | 4-Acetamidophenyl | 4-Acetamidophenyl | 432 | 338 |
| 67 | 1 | 4-Phenoxyphenyl | 4-Phenoxyphenyl | 417 | 408 |

-continued

| Example No. | Analogously to Example No. | R¹ | R² | $\lambda_{max}$ (nm) | FAB-MS (M⁺) |
|---|---|---|---|---|---|
| 68 | 1 | 4-Ethoxycarbonylphenyl | 4-Phenoxyphenyl | 410 | 388 |
| 69 | 2 | 4-Phenoxyphenyl | 4-Acetamidophenyl | 423 | 373 |
| 70* | 1 | 4-Phenoxyphenyl | 4-Phenoxyphenyl | 416 | 408 |
| 71 | 2 | 3-Methoxy-4-acetamidophenyl | 4-Phenoxyphenyl | 433 | 403 |
| 72 | 2 | 3,4-Diacetamidophenyl | 4-Phenoxyphenyl | 419 | 430 |
| 73 | 2 | 2,5-Dimethyl-4-acetamidophenyl | 4-Phenoxyphenyl | 394 | 401 |
| 74 | 2 | 2,4-Dimethoxyphenyl | 3,4-Diacetamidophenyl | 410 | 398 |
| 75 | 2 | 2,4-Diacetamidophenyl | 4-Acetamidophenyl | 408 | 368 |
| 76 | 1 | R¹ = 3,4-Dimethoxyphenyl, R² = 4-Phenoxyphenyl, R³ = Methyl | | 422 | 390 |
| 77 | 1 | R¹ = 3,4-Dimethoxyphenyl, R² = 4-Methoxyphenyl, R³ = Methyl | | 425 | 328 |
| 78 | 1 | R¹ = R² = 4-Methoxyphenyl, R³ = Methyl | | 414 | 289 |
| 79 | 1 | 4-Methoxyphenyl | 4-Methoxyphenyl | 423 | 284 |
| 80 | 1 | 4-Ethoxyphenyl | 4-Ethoxyphenyl | 425 | 348 |
| 81 | 1 | 4-Ethoxyphenyl | 4-Methoxyphenyl | 423 | 334 |
| 82 | 5 | 4-Nitrophenyl | 4-Nitrophenyl | 395 | 314 |
| 83 | 1 | 4-Nitrophenyl | 4-Tolyl | 404 | 283 |
| 84 | 1 | 4-Nitrophenyl | 4-Dimethylamino | 529 | 312 |
| 85 | 2 | 3,4-Diacetamidophenyl | 4-Methoxyphenyl | 425 | 368 |
| 86 | 2 | 2,5-Dimethyl-4-acetamidophenyl | 4-Methoxyphenyl | 399 | 339 |
| 87 | 2 | 2-Methoxy-5-acetamidophenyl | 4-Methoxyphenyl | 406 | 341 |
| 88 | 2 | 3-Methoxy-4-acetamidophenyl | 4-Methoxyphenyl | 434 | 341 |
| 89 | 2 | 2-Methyl-4-acetamidophenyl | 4-Methoxyphenyl | 402 | 325 |
| 90 | 2 | 2-Methyl-4-acetamidophenyl | 4-Phenoxyphenyl | 400 | 387 |
| 91 | 2 | 3-Methoxy-4-acetamidophenyl | 3-Methoxy-4-phenoxyphenyl | 419 | 371 |
| 92 | 2 | 3-Methoxy-4-acetamidophenyl | 4-Acetamidophenyl | 419 | 368 |
| 93 | 2 | 3,4-Diacetamidophenyl | 4-Acetamidophenyl | 427 | 395 |
| 94 | 2 | 2,5-Dimethyl-4-acetamidophenyl | 4-Acetamidophenyl | 419 | 366 |
| 95 | 1 | R¹ = 3,4-Dimethoxyphenyl, R² = 4-Methoxyphenyl, R³ = Methyl | | 425 | 328 |
| 96 | 5 | Phenyl | Phenyl | 385 | 224 |
| 97 | 5 | Phenyl | 4-Methoxyphenyl | 400 | 254 |

*in Example 70, X⁻ was a tosylate anion.

Example 98
Dyeing process for polyacrylonitrile 0.1 g of the dyestuff obtained according to Example 2 was made into a paste with 2 ml of water with the addition of a little acetic acid and dissolved with 50 ml of hot water. 1.2 g of a condensation product of naphthalenesulphonic acid and formaldehyde were then added and the mixture was topped up to 500 ml with cold water.

The pH of this dye liquor was brought to pH=4.5 to 5 with acetic acid and sodium acetate. 10 g of polyacrylonitrile fibres (piece goods) were agitated constantly in this dye liquor, while the temperature was increased to 100° C. in the course of 30 minutes. Dyeing was carried out at the boiling point for 60 minutes and the material was then rinsed with cold water and dried at 60° to 70° C. The material was dyed an intensive reddish-tinged yellow.

Example 99
Dyeing process for paper containing mechanical wood pulp

Dry pulp comprising 60% mechanical wood pulp and 40% non-bleached sulphite cellulose was beaten in a beater and refined to a degree of freeness of 40° SR with water in an amount such that the dry content was somewhat above 2.5%. A dry content of the thick pulp of exactly 2.5% was then established with water. 5 g of a 0.5% strength by weight aqueous solution of the dyestuff obtained according to Example 4 were added to 200 g of this thick pulp, the mixture was stirred for 5 minutes, 2% of resin size and 4% of alum, based on the dry pulp, were added and the mixture was again stirred homogeneously for a few minutes. The pulp was then diluted to 700 ml with water and sheets of paper were produced from this in a manner known per se by filtration with suction over a sheet former. The sheets showed an intensive yellow dyeing.

Example 100

Results analogous to those in Examples 98 and 99 were obtained using dyestuffs according to Examples 1, 3 and 5 to 97.

What is claimed is:

1. A method of dyeing or printing cationically dyeable fibers, tannin-treated cellulose materials, paper, silk or leather, which comprises applying to said cationically dyeable fiber, tannin-treated cellulose material, paper, silk or leather at least one 4,5-dihydro-1H-1,2,3-triazolium compound of the formula (I)

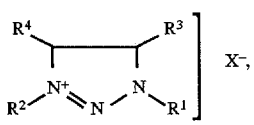 (I)

in which
- $R^1$ and $R^2$ independently of one another denote $C_6$–$C_4$-aryl or a heterocyclic radical having up to 3 rings and up to 4 heteroatoms from the series consisting of O, S and N,
- $R^3$ and $R^4$ independently of one another denote hydrogen, $C_1$–$C_{12}$-alkyl, $C_2$–$C_{12}$-alkenyl, $C_4$–$C_8$-cycloalkyl, $C_7$–$C_{17}$-aralkyl, $C_6$–$C_{14}$-aryl or nitrile or
- $R^3$ and $R^4$ together denote a 2- to 5-membered C bridge, which can optionally be interrupted by up to two oxygen or nitrogen atoms, and
- $X^-$ denotes an anion, wherein all the alkyl, alkenyl, cycloalkyl, aralkyl and aryl radicals and fused and heterocyclic radicals present can be unsubstituted or substituted by nonionic substituents, carboxyl groups, ammonium groups or pyridinium groups.

2. The method according to claim 1, in which formula (I),
- $R^1$ and $R^2$ independently of one another denote phenyl, naphthyl, thienyl, thiazolyl, isothiazolyl, 1,2,4-thiadiazolyl, 1,3,4-thiadiazolyl, benzothiazolyl, benzisothiazolyl, pyrazolyl, imidazolyl, benzimidazolyl, oxazolyl, benzoxazolyl, 1,2,3-triazolyl, 1,2,4-triazolyl, indolyl or pyridyl, wherein these radicals can be unsubstituted or substituted by up to 5 radicals from the group consisting of $C_1$–$C_8$-alkyl, $C_1$–$C_8$-alkoxy, $C_6$–$C_{10}$-aryloxy, $C_6$–$C_{10}$-arylamino, $C_7$–$C_{12}$-aralkylamino, $C_1$–$C_8$-acylamino, $C_1$–$C_8$-acyloxy, $C_1$–$C_8$-monoalkylamino, di-$C_1$–$C_8$-alkylamino, $C_1$–$C_8$-alkoxycarbonyl, $C_1$–$C_8$-alkoxycarbonyloxy, $C_1$–$C_{12}$-alkamidocarbonyl, $C_1$–$C_{12}$-alkylsulphonyl, $C_6$–$C_{10}$-arylazo, aminocarbonyl, halogen, cyano, hydroxyl, nitro, phenylsulphonyl, sulphonamide, sulphonamyl and ureido, which in their turn can be unsubstituted or substituted by hydroxyl, halogen, cyano or $C_1$–$C_4$-alkoxy,
- $R^3$ and $R^4$ independently of one another in each case denote hydrogen, $C_1$–$C_8$-alkyl, allyl, cyclopentyl or cyclohexyl which can be unsubstituted or substituted by hydroxyl, halogen, cyano, $C_1$–$C_4$-alkoxy, aminocarbonyl or $C_1$–$C_4$-alkoxycarbonyl, a benzyl, phenethyl, furyl, tetrahydrofurylmethyl, pyridyl, pyridylmethyl or pyridylethyl radical which are unsubstituted or substituted by halogen, cyano, $C_1$–$C_4$-alkyl and/or $C_1$–$C_4$-alkoxy, or a phenyl radical which are unsubstituted or substituted by halogen, cyano, $C_1$–$C_4$-alkyl or $C_1$–$C_4$-alkoxy or
- $R^3$ and $R^4$, together with the two carbon atoms in between, form a cyclobutane, cyclopentane, cyclohexane or cycloheptane ring which is unsubstituted or substituted by hydroxyl, halogen, cyano, $C_1$–$C_4$-alkoxy or aminocarbonyl and is not or is interrupted by a nitrogen atom, a tetrahydropyrrolidino or piperidino ring which is unsubstituted or substituted by hydroxyl, halogen, cyano, $C_1$–$C_4$-alkoxy or aminocarbonyl and is not or is interrupted by an oxygen atom, or a tetrahydrofuryl or tetrahydropyranyl ring which is unsubstituted or substituted by hydroxyl, halogen, cyano, $C_1$–$C_4$-alkoxy or aminocarbonyl and
- $X^-$ denotes an anion.

3. The method according to claim 1, in which the 4,5-dihydro-1H-1,2,3-triazolium compounds of the formula (I) correspond to the formula (II)

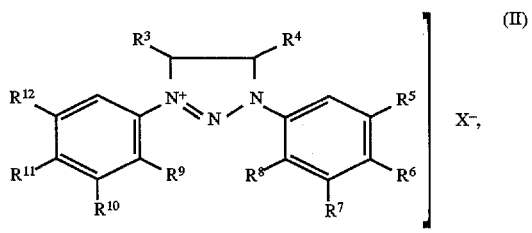 (II)

in which
- $R^3$ and $R^4$ independently of one another in each case denote hydrogen or a $C_1$–$C_4$-alkyl radical which is unsubstituted or substituted by hydroxyl, halogen, cyano, $C_1$–$C_4$-alkoxy, aminocarbonyl or $C_1$–$C_4$-alkoxycarbonyl or
- $R^3$ and $R^4$, together with the two carbon atoms in between, denote a cyclopentane or cyclohexane ring which is unsubstituted or substituted by hydroxyl, halogen, cyano, $C_1$–$C_4$-alkoxy or aminocarbonyl,
- $R^5$ to $R^{12}$ independently of one another in each case denote hydrogen or a $C_1$–$C_4$-alkyl, $C_1$–$C_4$-alkoxy, $C_6$–$C_{10}$-aryloxy, $C_6$–$C_{10}$-arylamino, $C_7$–$C_{12}$-aralkylamino, $C_1$–$C_4$-acylamino, $C_1$–$C_4$-acyloxy, $C_1$–$C_4$-monoalkylamino, di-$C_1$–$C_4$-alkylamino, $C_1$–$C_4$-alkoxycarbonyl, $C_1$–$C_4$-alkoxycarbonyloxy, $C_1$–$C_4$-alkamidocarbonyl, $C_1$–$C_4$-alkylsulphonyl or $C_6$-arylazo radical which is unsubstituted or substituted by hydroxyl, halogen, cyano or $C_1$–$C_4$-alkoxy, aminocarbonyl, halogen, cyano, hydroxyl, nitro, phenylsulphonyl, sulphonamide, sulphonamyl or ureido and
- $X^-$ denotes an anion.

4. The method according to claim 3, in which in the 4,5-dihydro-1H-1,2,3-triazolium compounds of the formula (II),
- $R^3$ and $R^4$ independently of one another denote hydrogen or methyl,
- $R^6$ denotes hydrogen, methyl, methoxy, ethoxy, phenoxy, acetylamino, dimethylamino, diethylamino, methoxycarbonyl, ethoxycarbonyl, aminocarbonyl, chlorine, cyano or nitro, in the case where $R^3$ and $R^4$ in each case denote hydrogen,
- $R^{11}$ denotes ethoxy, phenoxy, acetylamino, dimethylamino, diethylamino, methoxycarbonyl, ethoxycarbonyl, aminocarbonyl, chlorine, cyano or nitro, and in the case where at least one of the radicals $R^3$ and $R^4$ is other than hydrogen
- $R^{11}$ additionally can also denote hydrogen, methyl, methoxy or nitro,
- $R^5$ and $R^{12}$, and $R^7$ and $R^{10}$, in each case as pairs, are identical and denote hydrogen, methyl, methoxy, ethoxy, phenoxy, acetylamino, dimethylamino, diethylamino, methoxycarbonyl, ethoxycarbonyl, aminocarbonyl, chlorine, cyano or nitro,
- $R^8$ and $R^9$ independently of one another in each case denote hydrogen, methyl or methoxy and
- $X^-$ denotes an anion.

5. The method according to claim 3, in which in the 4,5-dihydro-1H-1,2,3-triazolium compounds of the formula (II),
- $R^3$, $R^5$, $R^8R^9$ and $R^{12}$ in each case denote hydrogen, $R^4$ denotes hydrogen or methyl, $R^6$ denotes methyl, methoxy, ethoxy, phenoxy, acetylamino, dimethylamino, diethylamino, methoxycarbonyl, ethoxycarbonyl or aminocarbonyl, in the case where $R^4$ denotes hydrogen, $R^{11}$ denotes ethoxy, phenoxy, acetylamino, dimethylamino, diethylamino, methoxycarbonyl, ethoxycarbonyl or aminocarbonyl, and in the case where $R^4$ denotes methyl, $R^{11}$ additionally can also denote hydrogen, methyl, methoxy or nitro, $R^7$ and $R^{10}$ independently of one another in each case denote hydrogen, methyl or methoxy and $X^-$ denotes an anion.

6. The method according to claim 1, wherein the cationically dyeable fibers, are polymers and copolymers of acrylonitril and the dyeing is carried out from a weakly acid liquor wherein the fibers are introduced into the dyebath at 40° C. to 60° C. and the dyeing is carried out at the boiling point or under pressure at temperatures above 100° C.

7. The method according to claim 1, wherein the cationically dyeable fibers are polymers and copolymers of acrylonitrile wherein in the compound of formula I is introduced into the spinning solution for the production of dyed fibers.

8. The method according to claim 1 wherein a paper containing mechanical wood pulp is dyed.

* * * * *

UNITED STATES PATENT AND TRADEMARK OFFICE
CERTIFICATE OF CORRECTION

PATENT NO. : 5,749,925
DATED : May 12, 1998
INVENTOR(S) : Bocker, et al.

It is certified that error appears in the above-indentified patent and that said Letters Patent is hereby corrected as shown below:

Col. 15, lines 8-9    Delete " $C_6-C_4$-aryl " and substitute -- $C_6-C_{14}$-aryl --

Signed and Sealed this

Sixteenth Day of March, 1999

Q. TODD DICKINSON

Attest:

Attesting Officer    Acting Commissioner of Patents and Trademarks